(12) United States Patent
Nguyen et al.

(10) Patent No.: US 7,040,314 B2
(45) Date of Patent: *May 9, 2006

(54) AEROSOL GENERATING DEVICES AND METHODS FOR GENERATING AEROSOLS SUITABLE FOR FORMING PROPELLANT-FREE AEROSOLS

(75) Inventors: Tung T. Nguyen, Midlothian, VA (US); Christopher L. Irving, Chesterfield, VA (US); Kenneth A. Cox, Powhatan, VA (US); Douglas D. McRae, Chesterfield, VA (US); Walter A. Nichols, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/653,934

(22) Filed: Sep. 4, 2003

(65) Prior Publication Data

US 2004/0081624 A1  Apr. 29, 2004

Related U.S. Application Data

(60) Provisional application No. 60/444,677, filed on Feb. 4, 2003, provisional application No. 60/408,280, filed on Sep. 6, 2002.

(51) Int. Cl.
*A61M 16/00* (2006.01)
(52) U.S. Cl. .................. 128/203.12; 128/200.14; 128/204.17
(58) Field of Classification Search .......... 128/203.12, 128/200.14, 200.22, 204.23, 204.17; 239/338
See application file for complete search history.

(56) References Cited

U.S. PATENT DOCUMENTS

| | | |
|---|---|---|
| 5,743,251 A | 4/1998 | Howell et al. |
| 5,934,272 A | 8/1999 | Lloyd et al. |
| 5,957,124 A | 9/1999 | Lloyd et al. |
| 6,030,682 A | 2/2000 | Marecki |
| 6,060,045 A | 5/2000 | Mettler |
| 6,098,620 A | 8/2000 | Lloyd et al. |
| 6,150,418 A | 11/2000 | Hochrainer et al. |
| 6,153,173 A | 11/2000 | Sapsford et al. |
| 6,234,167 B1 | 5/2001 | Cox et al. |
| 6,235,306 B1 | 5/2001 | Miranda et al. |
| 6,263,872 B1 | 7/2001 | Schuster et al. |
| 6,431,167 B1 | 8/2002 | Gonda et al. |
| 6,568,390 B1 | 5/2003 | Nichols et al. |
| 2002/0141944 A1 | 10/2002 | Freund et al. |
| 2004/0025865 A1* | 2/2004 | Nichols et al. |

OTHER PUBLICATIONS

Notification of Transmittal of the International Search Report or the Declaration for PCT/US03/27473 dated Jul. 22, 2004.

* cited by examiner

*Primary Examiner*—Mital Patel
(74) *Attorney, Agent, or Firm*—Buchanan Ingersoll PC

(57) ABSTRACT

Liquid aerosol formulations for generating aerosols include at least one high volatility carrier and a second component. In some embodiments, the liquid aerosol formulation is propellant free. An aerosol generating device generates an aerosol by passing liquid aerosol formulation through a flow passage heated to convert the liquid into a vapor, which is mixed with air to form an aerosol. In some embodiments, particles of the aerosol consist essentially of the second component. The aerosol generator can be incorporated in a hand held inhaler. The aerosol can be delivered to a targeted portion of the lung using the inhaler.

42 Claims, 10 Drawing Sheets ated U.S. Pat. Nos. 6,234,167 and 6,568,390 and commonly-assigned U.S. patent application Ser. No. 10/003,437 filed Dec. 6, 2001, each incorporated herein by reference in its entirety.

AEROSOL GENERATING DEVICES AND METHODS FOR GENERATING AEROSOLS SUITABLE FOR FORMING PROPELLANT-FREE AEROSOLS

This application claims priority under 35 U.S.C. § 119(e) to U.S. Provisional Application Nos. 60/444,677, filed Feb. 4, 2003, and 60/408,280, filed Sep. 6, 2002, which are incorporated herein by reference in their entirety.

BACKGROUND

Aerosols are gaseous suspensions of fine solid or liquid particles that are useful in a wide variety of applications. For example, medicated liquids may be administered in aerosol form. Medicated aerosols include materials that are useful in the treatment of respiratory ailments. In such applications, the aerosols may be produced by an aerosol generator and inhaled into a patient's lungs. Aerosols are also used in non-medicinal applications including, for example, industrial applications.

Aerosol generators are known that include a heated tube for vaporizing liquid. For example, commonly-assigned U.S. Pat. No. 5,743,251, which is incorporated herein by reference in its entirety, discloses an aerosol generator including a tube and a heater operable to heat the tube to a sufficient temperature to volatilize liquid in the tube. It is disclosed that the volatilized material expands out of an end of the tube and admixes with ambient air, thereby forming an aerosol.

As shown in FIG. 1, the aerosol generator 21 disclosed in the '251 patent includes a tube 23 defining a capillary-sized fluid passage and having an open end 25. The tube 23 also includes an inlet end 31 in fluid communication with a source 33 of liquid material. A heater 27 is positioned adjacent to the tube 23. The heater 27 is connected to a power supply 29. In operation, liquid is introduced into the tube 23. The heater 27 heats a portion of the tube 23 to a sufficiently high temperature to volatilize the liquid. The volatilized material expands out of the open end 25 of the tube and admixes with ambient air. When it is desired to generate an aerosol for drug inhalation, the aerosol generator 23 is preferably provided with a puff-actuated sensor 37 (shown by dotted lines), which preferably forms part of a mouthpiece 39 (shown by dotted lines) disposed proximate the open end 25 of the tube 23.

Other aerosol generators including a heated tube for vaporizing liquids to produce an aerosol are described in commonly-assigned U.S. Pat. Nos. 6,234,167 and 6,568,390 and commonly-assigned U.S. patent application Ser. No. 10/003,437 filed Dec. 6, 2001, each incorporated herein by reference in its entirety.

SUMMARY

Liquid aerosol formulations for producing aerosols are provided. The liquid aerosol formulations preferably comprise a high volatility liquid carrier and a second component. In addition, aerosol generating devices and methods for generating aerosols are provided.

The high volatility liquid carrier is heated to produce an aerosol having a desired particle size. According to a preferred embodiment, the high volatility liquid carrier can be heated to form a vapor that does not form an appreciable condensation aerosol when the vapor is admixed with cooler air. That is, the vapor of the high volatility liquid remains substantially in vapor form when admixed with the cooler air. The second component, however, may or may not form a vapor when the liquid carrier is volatilized. Thus, an aerosol is formed from particles of the second component or from condensed vapor of the second component when the vapor is admixed with the cooler air. By vaporizing the liquid aerosol formulation and then admixing the vapor with cooler air the resulting aerosol comprises aerosol particles that are substantially particles of only the second component (i.e., the aerosol particles consist essentially of only the second component). Preferred second components are medicaments such as albuterol and budesonide. Preferred liquid aerosol formulations comprise a medicament dissolved in a high volatility carrier to form a solution.

In a further preferred embodiment, the liquid aerosol formulation is propellant free. Further, the liquid aerosol formulation is preferably a solution. In such preferred embodiments, the second component is a solute, which is dissolved in the liquid carrier. The high volatility carrier, which can comprise ethanol, water, acetone, ethyl acetate, hexanes, other alcohols such as isopropanol, butanol, or mixtures thereof, preferably has a boiling point of 100° C. or less.

An embodiment of an aerosol generating device for generating an aerosol comprises a liquid source and a flow passage in fluid communication with the liquid source. The liquid source contains a liquid aerosol formulation including a high volatility carrier and a second component. A heater is disposed to heat liquid in the flow passage to produce vapor. The vapor exits an outlet end of the flow passage and is admixed with air to produce an aerosol.

An exemplary embodiment of a method of generating an aerosol comprises supplying a liquid comprising a high volatility carrier and a second component to a flow passage, and heating liquid in the flow passage to produce a vapor, which exits the flow passage. The vapor is admixed with air to produce an aerosol with a desired particle size. A preferred flow passage is a capillary-sized flow passage.

DETAILED DESCRIPTION OF PREFERRED EMBODIMENTS

Figure 1:
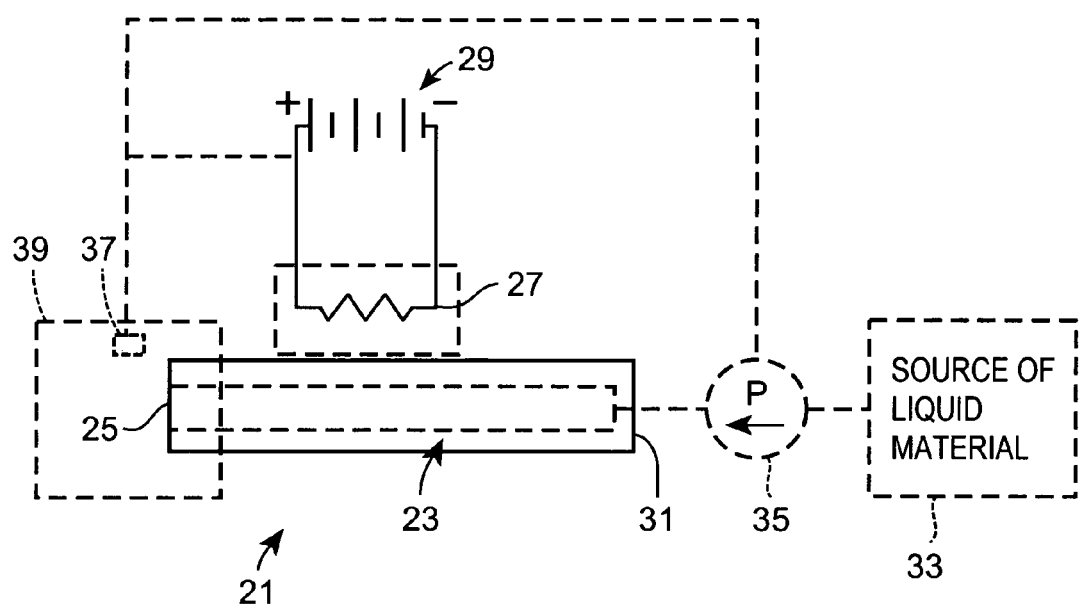
FIG. 1 illustrates an aerosol generator having a heated capillary passage according to the prior art.

Liquid aerosol formulations, aerosol generating devices and methods for generating aerosols from the liquid aerosol formulations are provided.

The liquid aerosol formulations, which can produce aerosols having selected compositions and controlled particle sizes, are suitable for different applications. For example, for drug delivery applications via inhalation, the liquid aerosol formulations can be used to produce aerosols having a desirable mass median aerodynamic diameter (MMAD) for targeted delivery. "Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

In preferred embodiments, the liquid aerosol formulations can be used to produce aerosols of drug formulations having a controlled particle size that is effective to achieve pulmonary delivery, tracheobronchial delivery or delivery to the oropharynx or mouth. Typically, for pulmonary delivery particles of smaller size are desired than for tracheobronchial or oral delivery.

In further embodiments, the liquid aerosol formulations can be used to produce bulk quantities of particles for pharmaceutical or industrial applications. Exemplary industrial applications include producing dry particles for coatings, and producing particles of solid materials (e.g., metals, metal oxides and/or alloys) for various uses including micro ball bearings, foam metals and microelectronic applications. For example, particles can be used in abrasive media for fine polishing and as components of fertilizers or lubricants.

The liquid aerosol formulations include at least one high volatility carrier and at least one second component. In a preferred embodiment, the carrier is a liquid solvent and the second component is a solute dissolved in the liquid carrier. However, the liquid aerosol formulation can be a suspension, dispersion, gel or an emulsion of the second component in the high volatility carrier(s).

In a preferred embodiment, the liquid aerosol formulation is propellant free, and the liquid aerosol formulation is vaporized by heating and aerosolized by contacting the resulting vapor with air. The air is preferably ambient air.

As used herein, the term "high volatility carrier" denotes a liquid that has a boiling point higher than 25° C. and remains substantially in the vapor state when it is vaporized by heating and the resulting vapor is admixed with ambient air. The second component of the liquid aerosol formulation, however, forms an aerosol when the liquid aerosol formulation is vaporized and admixed with ambient air. By combining at least one high volatility carrier and second component, in a preferred embodiment, the liquid aerosol formulations can be used to produce aerosols containing liquid and/or solid aerosol particles that are substantially particles of only the second component, i.e., aerosol particles that are substantially free of the high volatility carrier.

The high volatility carriers have a low boiling point. In a preferred embodiment, the high volatility carriers have a boiling point of 100° C. or less, where 100° C. is the boiling point of water at atmospheric pressure. A preferred high volatility carrier is ethyl alcohol (ethanol), which has a boiling point of about 78° C. at a pressure of 1 atmosphere. Ethanol can be used in combination with other liquids, e.g., ethanol/water solutions containing 1 to 10 volume % water. In other preferred embodiments, the liquid aerosol formulation can contain as the carrier about 20 to 80 volume % water and about 80 to 20 volume % ethanol, or about 80–100 volume % water and up to about 20 volume % ethanol. Ethanol is a Federal Drug Administration (FDA) accepted excipient in drug products administered via inhalation.

Ethanol and other suitable high volatility carriers can be used as solvents for liquid aerosol formulations, such as drug formulations, which form an aerosol when heated into a vapor state and the vapor is admixed with air. Preferably, the carrier is present substantially only in the vapor state, i.e., substantially no aerosol of the carrier is formed. Accordingly, the aerosol particles in such aerosols are substantially only particles of the second component. When the liquid aerosol formulation is a solution and the second component is a solute, in a preferred embodiment, the aerosol particles are substantially only the solute, i.e., consist essentially of the solute. Ethanol is converted from a liquid to a vapor by heating the liquid aerosol formulation to a sufficiently high temperature (e.g., to a temperature greater than the boiling point of ethanol). In a preferred embodiment, the concentration of ethanol in the aerosol produced from the liquid aerosol formulation is below the saturation limit of ethanol in air with which the ethanol is admixed so that ethanol vapor substantially does not convert to an aerosol. Consequently, ethanol remains substantially in the vapor phase when used to form aerosols for delivery via inhalation or when used to form bulk volumes of dry particles.

As described above, liquids other than ethanol that have a high volatility can be used as a carrier in the liquid aerosol formulations. In a preferred embodiment, a liquid carrier that has a high volatility, but is not an FDA accepted excipient in drugs administered via inhalation, can be used in the liquid aerosol formulations for applications other than delivering drugs via such inhalation. Such other high volatility (i.e., non-condensing) liquids can include, but are not limited to, water, acetone, ethyl acetate, hexanes, other alcohols, such as isopropanol, butanol and mixtures thereof. The liquid carrier can comprise a hydrophilic liquid or a hydrophobic liquid. These liquids can be used as a carrier in the liquid aerosol formulation to produce aerosols that contain liquid and/or solid aerosol particles that are substantially particles of only the second component of the liquid aerosol formulation.

Various substances can be used as the second component in the liquid aerosol formulations, depending on the desired application of the liquid aerosol formulation. For example, the second component can be any suitable medicament that can be delivered to a patient by an aerosol. Exemplary suitable medicaments include, but are not limited to, one of the following classes: analgesics; anginal preparations; antiallergics; antibiotics; anti-convulsants; antidepressants; antiemetics; antihistamines; antiparkisonian drugs; antipsychotics; antitussives; anxiolytics; bronchodilators; diuretics;

anticholinergics; hormones and anti-flammatory agents, such as those described in U.S. Pat. No. 6,153,173, which is incorporated herein by reference in its entirety; drugs for erectile dysfunction; drugs for migraine headaches; drugs for the treatment of alcoholism; drugs for the treatment of addiction; muscle relaxants; nonsteroidal anti-inflammatories; opioids and other stimulants. The liquid aerosol formulation can be selected to provide a desired dose of the medicament via aerosol inhalation.

Typically, where the medicament is an antibiotic, it is selected from one of the following compounds: cefinetazole; cefazolin; cephalexin; cefoxitin; cephacetrile; cephaloglycin; cephaloridine; cephalosporins, such as cephalosporin C; cephalotin; cephamycins, such as cephamycin A, cephamycin B, and cephamycin C; cepharin; cephradine; ampicillin; amoxicillin; hetacillin; carfecillin; carindacillin; carbenicillin; amylpenicillin; azidocillin; benzylpenicillin; clometocillin; cloxacillin; cyclacillin; lipopeptides; methicillin; nafcillin; 2-pentenylpenicillin; penicillins, such as penicillin N, penicillin O, penicillin S, penicillin V; chlorobutin penicillin; dicloxacillin; diphenicillin; heptylpenicillin; and metampicillin.

Typically, where the medicament is an anticonvulsant, it is selected from one of the following compounds: benzodiazepine, gabapentin, tiagabine, and vigabatrin.

Typically, where the medicament is an antidepressant, it is selected from one of the following compounds: amitriptyline, amoxapine, benmoxine, butriptyline, clomipramine, desipramine, dosulepin, doxepin, imipramine, kitanserin, lofepramine, medifoxamine, mianserin, maprotoline, mirtazapine, nortriptyline, protriptyline, trimipramine, viloxazine, citalopram, cotinine, duloxetine, fluoxetine, fluvoxamine, milnacipran, nisoxetine, paroxetine, reboxetine, sertraline, tianeptine, acetaphenazine, binedaline, brofaromine, cericlamine, clovoxamine, iproniazid, isocarboxazid, moclobemide, phenyhydrazine, phenelzine, selegiline, sibutramine, tranylcypromine, ademetionine, adrafinil, amesergide, amisuipride, amperozide, benactyzine, bupropion, caroxazone, gepirone, idazoxan, metralindole, milnacipran, minaprine, nefazodone, nomifensine, ritanserin, roxindole, S-adenosylmethionine, tofenacin, trazodone, tryptophan, venlafaxine, and zalospirone.

Typically, where the medicament is an antiemetic, it is selected from one of the following compounds: alizapride, azasetron, benzquinamide, bromopride, buclizine, chlorpromazine, cinnarizine, clebopride, cyclizine, diphenhydramine, diphenidol, dolasetron methanesulfonate, droperidol, granisetron, hyoscine, lorazepam, metoclopramide, metopimazine, ondansetron, perphenazine, promethazine, prochlorperazine, scopolamine, triethylperazine, trifluoperazine, triflupromazine, trimethobenzamide, tropisetron, domeridone, and palonosetron.

Typically, where the medicament is an antihistamine, it is selected from one of the following compounds: azatadine, brompheniramine, chlorpheniramine, clemastine, cyproheptadine, dexmedetomidine, diphenhydramine, doxylamine, hydroxyzine, cetrizine, fexofenadine, loratidine, and promethazine.

Typically, where the medicament is an antiparkisonian drug, it is selected one of the following compounds: amantadine, baclofen, biperiden, benztropine, orphenadrine, procyclidine, trihexyphenidyl, levodopa, carbidopa, selegiline, deprenyl, andropinirole, apomorphine, benserazide, bromocriptine, budipine, cabergoline, dihydroergokryptine, eliprodil, eptastigmine, ergoline pramipexole, galanthamine, lazabemide, lisuride, mazindol, memantine, mofegiline, pergolike, pramipexole, propentofylline, rasagiline, remacemide, spheramine, terguride, entacapone, and tolcapone.

Typically, where the medicament is an antipsychotic, it is selected from one of the following compounds: acetophenazine, alizapride, amperozide, benperidol, benzquinamide, bromperidol, buramate, butaperazine, carphenazine, carpipramine, chlorpromazine, chlorprothixene, clocapramine, clomacran, clopenthixol, clospirazine, clothiapine, cyamemazine, droperidol, flupenthixol, fluphenazine, fluspirilene, haloperidol, mesoridazine, metofenazate, molindrone, penfluridol, pericyazine, perphenazine, pimozide, pipamerone, piperacetazine, pipotiazine, prochlorperazine, promazine, remoxipride, sertindole, spiperone, sulpiride, thioridazine, thiothixene, trifluperidol, triflupromazine, trifluoperazine, ziprasidone, zotepine, zuclopenthixol, amisulpride, butaclamol, clozapine, melperone, olanzapine, quetiapine, and risperidone.

Typically, where the medicament is a drug that is an anxiolytic, it is selected from one of the following compounds: mecloqualone, medetomidine, metomidate, adinazolam, chlordiazepoxide, clobenzepam, flurazepam, lorazepam, loprazolam, midazolam, alpidem, alseroxlon, amphenidone, azacyclonol, bromisovalum, buspirone, calcium N-carboamoylaspartate, captodiamine, capuride, carbcloral, carbromal, chloral betaine, enciprazine, flesinoxan, ipsapiraone, lesopitron, loxapine, methaqualone, methprylon, propanolol, tandospirone, trazadone, zopiclone, and zolpidem. Aerosol particles can be formed from sedative-hypnotics such as zaleplom, zopiclone, and zolpidem.

Typically, where the medicament is a drug for erectile dysfunction, it is selected from one of the following compounds: cialis (IC351), sildenafil, vardenafil, apomorphine, apomorphine diacetate, phentolamine, and yohimbine. Medicament particles for treating sexual dysfunction in a female individual, comprising administering to the vagina, vulvar area or urethra of the individual a pharmaceutical formulation that comprises an effective amount of a vasoactive agent selected from the group consisting of naturally occurring prostaglandins, synthetic prostaglandin derivatives, endothelial-derived relaxation factors, vasoactive intestinal polypeptide agonists, smooth muscle relaxants, leukotriene inhibitors, calcium channel blockers, phosphodiesterase inhibitors, nitrates, α-receptor blocking agents, ergotamine drugs, antihypertensive agents, pharmacologically acceptable salts, esters, analogs, derivatives, prodrugs and inclusion complexes of any of the foregoing, and combinations thereof.

Typically, where the medicament is a drug for migraine headache, it is selected from one of the following compounds: ahnotriptan, alperopride, codeine, dihydroergotamine, ergotamine, eletriptan, frovatriptan, isometheptene, lidocaine, lisuride, metoclopramide, naratriptan, oxycodone, propoxyphene, rizatriptan, sumatriptan, tolfenamic acid, zolmitriptan, amitriptyline, atenolol, clonidine, cyproheptadine, diltiazem, doxepin, fluoxetine, lisinopril, methysergide, metoprolol, nadolol, nortriptyline, paroxetine, pizotifen, pizotyline, propanolol, protriptyline, sertraline, timolol, and verapamil.

Typically, where the medicament is a drug for the treatment of alcoholism, it is selected from one of the following compounds: naloxone, naltrexone, and disulfiram.

Typically, where the medicament is a drug for the treatment of addiction it is buprenorphine.

Typically, where the medicament is a muscle relaxant, it is selected from one of the following compounds: baclofen, cyclobenzaprine, orphenadrine, quinine, and tizanidine.

Typically, where the medicament is a nonsteroidal anti-inflammatory, it is selected from one of the following compounds: aceclofenac, alminoprofen, amfenac, aminopropylon, amixetrine, benoxaprofen, bromfenac, bufexamac, carprofen, choline, salicylate, cinchophen, cinmetacin, clopriac, clometacin, diclofenac, etodolac, indoprofen, mazipredone, meclofenamate, piroxicam, pirprofen, and tolfenamate.

Typically, where the medicament is an opioid, it is selected from one of the following compounds: alfentanil, allylprodine, alphaprodine, anileridine, benzylmorphine, bezitramide, buprenorphine, butorphanol, carbiphene, cipramadol, clonitazene, codeine, dextromoramide, dextropropoxyphene, diamorphine, dihydrocodeine, diphenoxylate, dipipanone, fentanyl, hydromorphone, L-alpha acetyl methadol, lofentanil, levorphanol, meperidine, methadone, meptazinol, metopon, morphine, nalbuphine, nalorphine, oxycodone, papaveretum, pethidine, pentazocine, phenazocine, remifentanil, sufentanil, and tramadol.

Typically, where the medicament is an other analgesic it is selected from one of the following compounds: apazone, benzpiperylon, benzydramine, caffeine, clonixin, ethoheptazine, flupirtine, nefopam, orphenadrine, propacetamol, and propoxyphene.

Typically, where the medicament is a stimulant, it is selected from one of the following compounds: amphetamine, brucine, caffeine, dexfenfluramine, dextroamphetamine, ephedrine, fenfluramine, mazindol, methyphenidate, pemoline, phentermine, and sibutramine.

If desired, medicament particles can be formed from esters of antibiotics; esters of anticonvulsants; esters of antidepressants; esters of antihistamines; esters of antiparkinsonian drugs; esters of drugs for migraine headaches; esters of drugs for the treatment of alcoholism; esters of muscle relaxants; esters of anxiolytics; esters of nonsteroidal anti-inflammatories; esters of other analgesics; and, esters of steroids.

Medicament particles can comprise physiologically active compounds comprising chlordiazepoxide, betahistine, clonidine, testosterone, conjugated estrogens, estrogen esters, estradiol, estradiol esters, ethinyl estradiol, ethinyl estradiol esters, or hyoscyamine.

Medicament particles for treating anxiety can comprise alprazolam, estazolam, midazolam and triazolam.

Medicament particles can be generated for treating stroke, promoting angiogenesis, promoting collateral blood vessel formation, promoting nerve regeneration, promoting wound healing, treating or preventing a nervous system disease, i.e., a central nervous system disease or a peripheral nervous system disease, or preventing myocardial damage in heart disease and surgery.

Medicament particles can comprise beta-blockers comprising atenolol, pindolol, esmolol, propanolol or metoprolol. Medicament particles can comprise antibacterial agents comprising lipopeptide compounds.

Medicament particles can comprise polysaccharides such as glycosaminoglycan, a heparin, a heparin sulfate, a low molecular weight heparin, a biotechnology derived heparin, a chemically modified heparin, a heparin mimetic (e.g., a monosaccharide, oligosaccharide or polysaccharide that has at least one heparin-like function such as AT-III binding), or an unfractionated heparin preparation.

In a preferred embodiment, the medicament in the liquid aerosol formulation is albuterol or budesonide, which are used for the treatment of asthma. Both albuterol and budesonide are sufficiently soluble in ethanol to form solutions at ambient conditions. Ethanol solutions of albuterol or budesonide can be provided in different compositions. For example, a 1% albuterol (or budesonide)/ethanol solution can be used to produce aerosols for delivering a therapeutically effective dose of the medicament via inhalation. The concentration of the medicament in the solution can be varied to control the amount of the medicament in such aerosols. For example, the liquid aerosol formulation can comprise greater than about 0.1 wt./wt. % medicament mixed with the high volatility carrier (e.g., 0.2, 0.5, 1, 2, 4, 10, 20, 30 wt./wt. % or greater). According to an embodiment, a solution of a medicament in ethanol can be used to produce dry particles of the medicament. A bulk volume of dry particles of the medicament can be incorporated in various drug delivery formulations (e.g., capsules for oral administration, liquids for injection or ointments for topical administration).

Solutions of albuterol or budesonide can also be formed using a carrier including ethanol and water. In addition, solutions can be formed using only water as the high volatility carrier.

The liquid aerosol formulation can include a non-medicament. For example, in a preferred embodiment, the liquid aerosol formulation may include another type of substance, such as components used in paints, scents or fuels for research, commercial or industrial applications.

As mentioned above, the at least one high volatility carrier and second component can alternatively be provided in a suspension comprising solid particles in a liquid, i.e., solid particles of the second component in the high volatility liquid carrier. As with the above-described solutions, such suspensions can be heated to form an aerosol that contains liquid and/or solid aerosol particles that are substantially particles of only the second component.

In embodiments in which the liquid aerosol formulations are used to form aerosols for other purposes, such as industrial applications, different second components can be used in the liquid aerosol formulations depending on the desired composition of the aerosol particles. If desired, more than one second component may be used in the liquid aerosol formulation.

In a preferred embodiment, the liquid aerosol formulation is flowed through a capillary-sized flow passage in which the liquid is heated to a sufficiently high temperature to vaporize the liquid. The vapor exits the flow passage and admixes with gas, typically ambient air, to produce an aerosol that preferably is substantially aerosol particles of the second component, which is inhaled by a user. The size of the aerosol particles thus produced can be controlled for delivery to the lung.

Compared to propellant-assisted aerosol generators, which produce a high velocity ballistic stream, the low velocity jet that emerges from an open end of a heated capillary passage can deliver a medicated dose of an aerosol over a longer time, e.g., greater than 1 second, more preferably at least 2 seconds, which permits greater coordination between the formation and inhalation of the aerosol in embodiments where the aerosol comprises a medicated dose for inhalation by a user.

Figure 2:
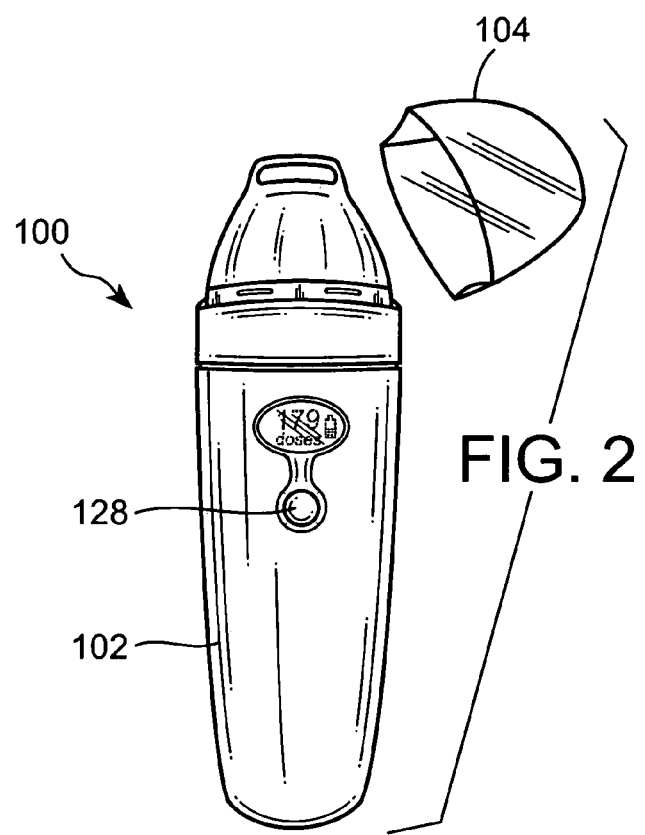
FIG. 2 is a perspective view of an embodiment of an aerosol generating device with the cap removed.
Figure 3:
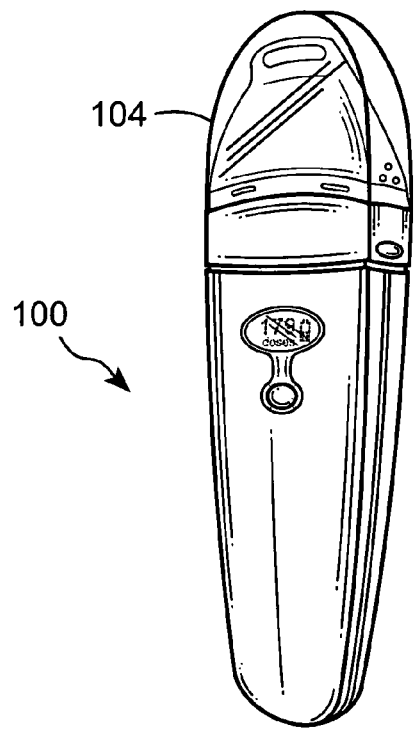
FIG. 3 shows the aerosol generating device of FIG. 2 with the cap installed.
Figure 4:
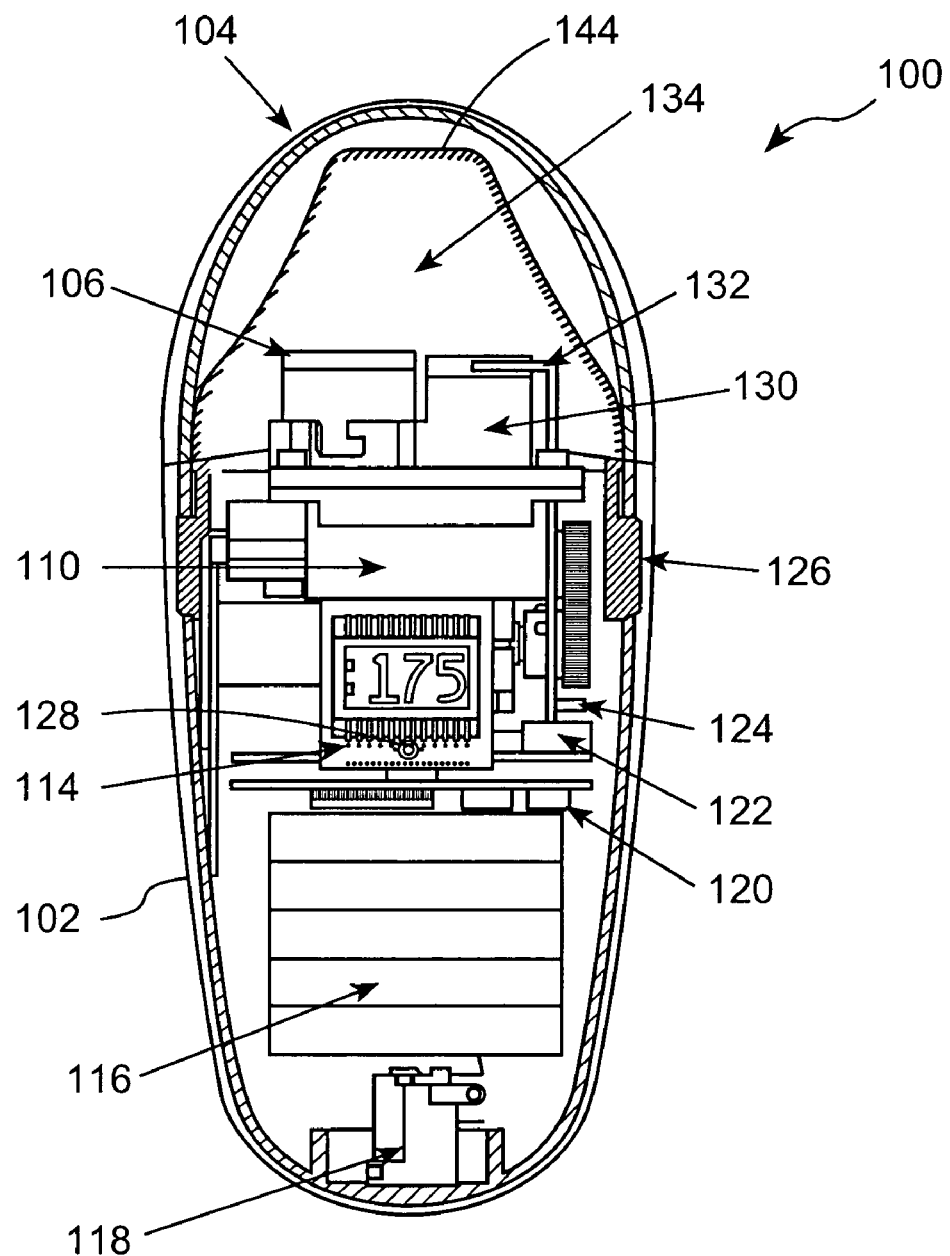
FIG. 4 illustrates an embodiment of an aerosol generating device.

The high volatility liquid aerosol formulation can be aerosolized using the aerosol generator shown in FIG. 1. FIGS. 2–4 illustrate an exemplary embodiment of another aerosol generating device 100 that can be used to produce aerosols of the liquid aerosol formulation for delivery via inhalation. The aerosol generating device 100 includes a housing 102; a removable protective cap 104, which activates a master on/off switch, (not shown); a fluid delivery assembly 110 including a liquid source 106 and a heater unit 130; a display 114; a battery unit 116; a charging jack 118; control electronics 120; a pressure sensor 122; an air inlet 124; a release 126 for detaching the fluid delivery assembly 110 from the aerosol generating device 100; a manually actuated master activation switch 128; an air passage 132 and a removable mouthpiece 134. FIG. 2 shows the cap 104 removed from the aerosol generating device 100, while FIG. 3 shows the cap installed.

In a preferred embodiment, the fluid delivery assembly 110 is removably attachable to a portion of the aerosol generating device 100 by any suitable attachment construction (e.g., snap-on, twist-on, etc.). For example, conductive contacts (not shown) can be provided in the aerosol generating device to make electrical contact with the heater unit 130 when the fluid delivery assembly 110 is attached to the aerosol generating device. In such embodiments, the fluid delivery assembly 110, which includes the wetted components of the aerosol generating device, can be replaced in the vapor generating device as a complete unit. As described below, the fluid delivery assembly 110 can provide aerosols having a controlled particle size. Different fluid delivery assemblies 110 that can provide aerosols having different compositions and/or particle sizes can be interchanged in the aerosol generating device.

The fluid delivery assembly 110 can be removed and replaced after liquid contained in the liquid source 106 has been consumed. A fluid delivery assembly 110 including a liquid source containing the same or a different medicament, and that produces the same or a different aerosol particle size, can then be installed in the aerosol generating device.

Figure 5:
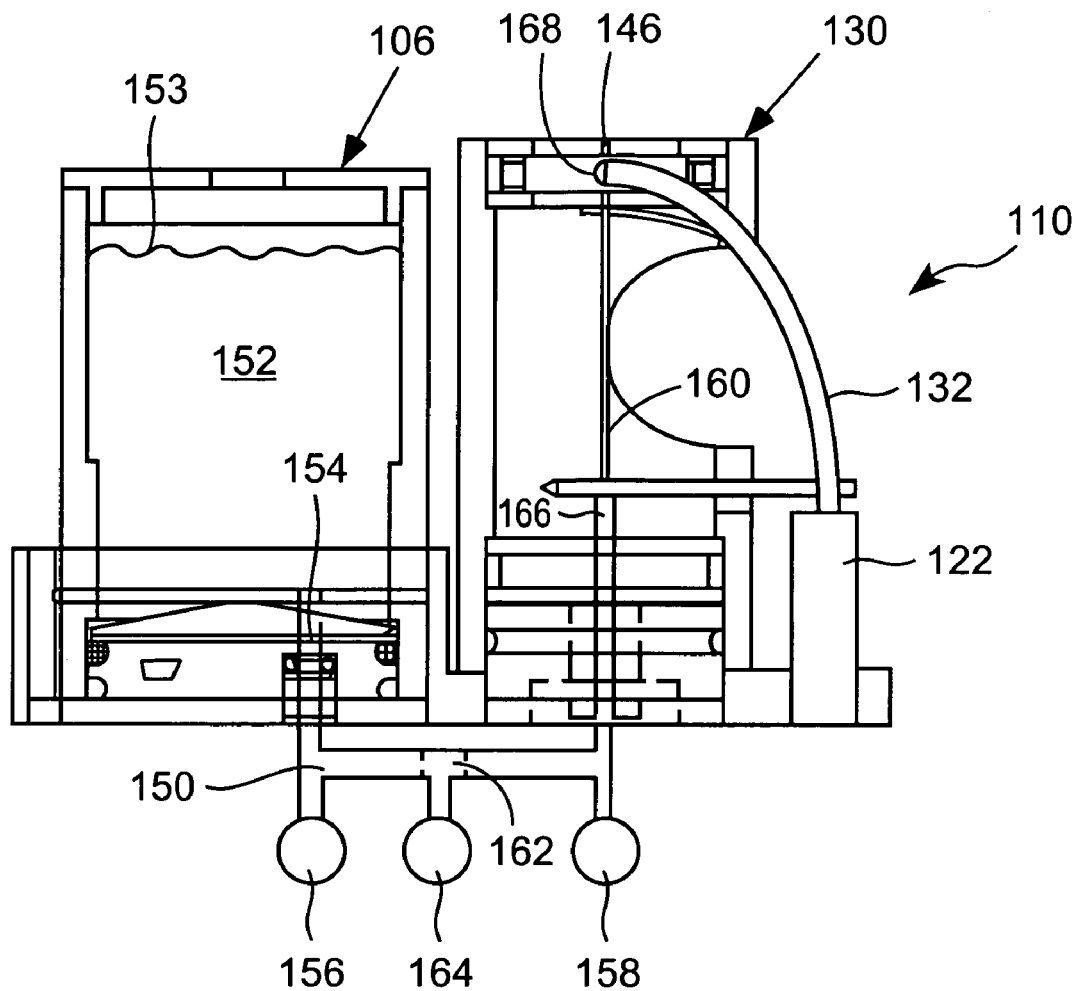
FIG. 5 illustrates an embodiment of the fluid delivery assembly of the aerosol generating device.

FIG. 5 illustrates a portion of the fluid delivery assembly 110, including a liquid source 106 and heater unit 130. Liquid is supplied from the liquid source 106 to the heater unit 130 through a flow passage 150.

The liquid source 106 comprises a reservoir 152 for containing a volume of liquid 153. In an embodiment, the liquid source 106 has a liquid capacity for delivering a selected number of doses of a selected volume. For example, the doses can be 5 µL doses and the reservoir 152 can be sized to contain multiple doses. Preferably, the liquid source can contain from about 10 doses to about 500 doses, e.g., 50 to 250 doses. However, the dose capacity of the liquid source can be determined by the desired application of the aerosol generating device. The liquid contained in the liquid source can be any liquid aerosol formulation that can be vaporized and aerosolized in the aerosol generating device to produce a desired aerosol as described above. In a preferred embodiment, the liquid contains a medicament formulated to be inhaled into the user's lungs in aerosol form.

The liquid source 106 includes an upstream flow passage 154 that provides fluid communication from the reservoir 152 to the flow passage 150. The aerosol generating device 100 preferably includes at least one valve disposed to control flow of the liquid from the liquid source 106 into the heater unit 130. For instance, the aerosol generating device may include a single valve (not shown) or a plurality of valves to control flow of the liquid in the flow passage. In a preferred embodiment, the aerosol generating device includes an inlet valve 156 and an outlet valve 158. The inlet valve 156 is operable to open and close an inlet of the flow passage 150, which controls the supply of liquid from the liquid source 106 into the flow passage 150. The outlet valve 158 is operable to open and close an outlet end of the flow passage 150, which controls the supply of liquid from the flow passage 150 into a heated flow passage 160.

The aerosol generating device 100 preferably includes a metering chamber 162 located in the flow passage 150 between the inlet valve 156 and the outlet valve 158. The metering chamber 162 is preferably sized to contain a predetermined volume of the liquid, such as a volume of the liquid that corresponds to one dose of the aerosolized medicament. A discharge member 164 can be used to open the metering chamber 162 during a liquid filling cycle, and to empty the metering chamber during a liquid delivery cycle, as described in greater detail below.

The heater unit 130 of the fluid delivery assembly 110 comprises a heated flow passage 160. The heated flow passage 160 is preferably a capillary sized flow passage, referred to hereinafter as a "capillary passage." The capillary passage 160 forms a portion of the entire flow passage in the aerosol generating device 100. The capillary passage 160 includes an open inlet end 166, and an opposite open outlet end 168. During operation of the aerosol generating device 100, liquid is supplied into the capillary passage 160 at the inlet end 166 from the flow passage 150.

The capillary passage 160 can have different transverse cross-sectional shapes (e.g., irregular shapes or regular shapes such as round, oval, triangular, square, rectangular, etc.). Different portions of the capillary passage can have different cross-sectional shapes. The size of the capillary passage 160 can be defined by a transverse dimension or by its transverse cross-sectional area. For example, the capillary passage can have a maximum transverse dimension of 0.01 to 10 mm, preferably 0.05 to 1 mm, and more preferably 0.1 to 0.5 mm. The capillary passage can be have a transverse cross sectional area of about $8 \times 10^{-5}$ to 80 mm$^2$, preferably about $2 \times 10^{-3}$ to $8 \times 10^{-1}$ mm$^2$, and more preferably about $8 \times 10^{-3}$ to $2 \times 10^{-1}$ mm$^2$.

As an example, the capillary passage can comprise a stainless steel tube having electrical leads attached thereto for passage of a DC current through the tube. The stainless steel tube can have any desired diameter. A 32 gauge tube has an internal diameter of 0.11 mm (0.004 inch) and a 26 gauge tube has an internal diameter of 0.26 mm (0.01 inch). If a higher flow rate of liquid is desired, a larger sized flow passage can be used to volatilize the liquid. Although a stainless steel tube can be used as a combination capillary passage/heater, other arrangements can be used for the capillary passage/heater arrangement.

As described in commonly-assigned U.S. Provisional Patent Application No. 60/408,295, filed Sep. 6, 2002, which is incorporated herein by reference in its entirety, embodiments of the capillary passage 160 can comprise an outlet section, which controls the velocity of vapor exiting the outlet end 168 of the capillary passage, i.e., the exit velocity of the vapor, so as to control the particle size of aerosol generated by the aerosol generating device 100.

The material forming the capillary passage can be any suitable material, including metals, plastics, polymers, ceramics, glasses, or combinations of these materials. Preferably, the material is a heat-resistant material capable of withstanding the temperatures, repeated heating cycles and pressures used to generate multiple doses of aerosols. In addition, the material forming the capillary passage preferably is non-reactive with the liquid that is aerosolized.

The capillary passage can be formed in a polymer, glass, metal and/or ceramic monolithic or multilayer (laminated) structure (not shown). Suitable ceramic materials for forming the capillary passage include, but are not limited to, alumina, zirconia, silica, aluminum silicate, titania, yttria-stabilized zirconia, or mixtures thereof. A capillary passage can be formed in the monolithic or multilayer body by any suitable technique, including, for example, machining, molding, extrusion, or the like.

In embodiments, the capillary passage can have a length from 0.5 to 10 cm, and preferably from 1 to 4 cm.

Figure 6:
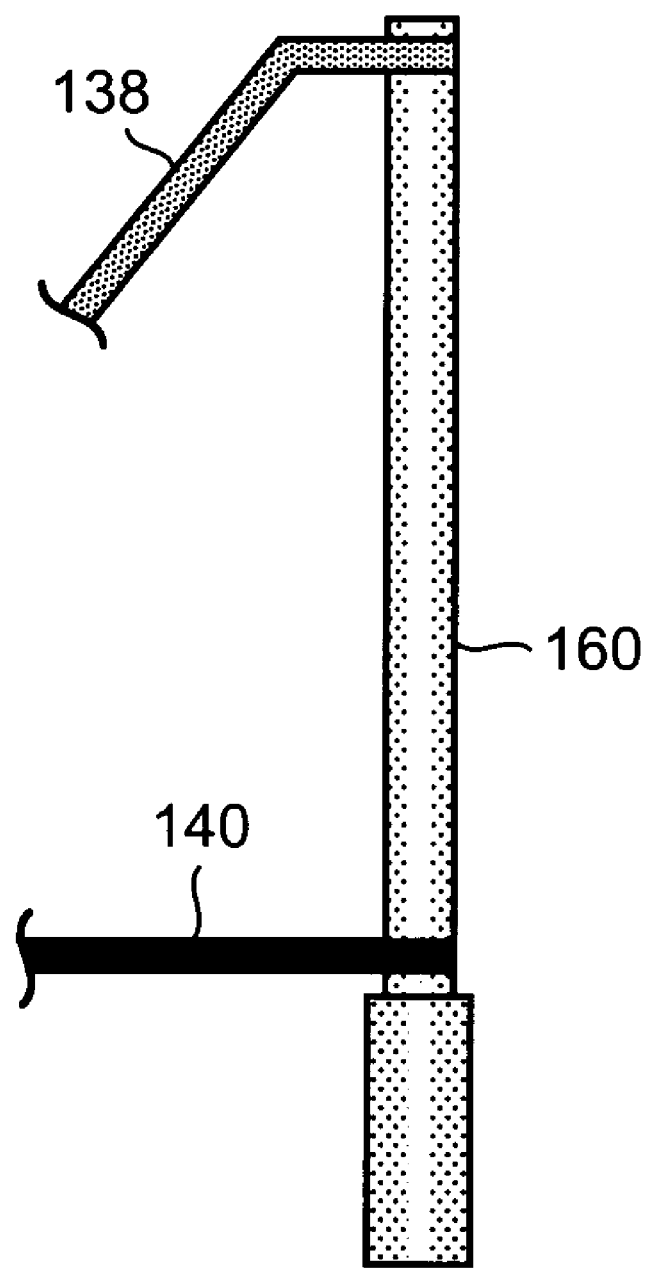
FIG. 6 illustrates an embodiment of the capillary passage including two electrodes.

The fluid supplied from the liquid source 106 is heated in the capillary passage to form a vapor during operation of the aerosol generating device 100. In a preferred embodiment shown in FIG. 6, the capillary 160 comprises metal tubing heated by passing an electrical current along a length of the capillary via a first electrode 138 and a second electrode 140. However, as described above, the capillary passage can have other alternative constructions, such as a monolithic or multi-layer construction, which include a heater such as a resistance heating material positioned to heat the fluid in the capillary passage. For example, the resistance heating material can be disposed inside of, or exterior to, the capillary passage.

The capillary passage 160 may comprise an electrically conductive tube provided with the electrode 138 (i.e., downstream electrode), and the electrode 140 (i.e., upstream electrode). Upstream electrode 140 is preferably made of copper or a copper-based material, while downstream electrode 138 preferably is made of a higher resistance material, such as stainless steel. In this embodiment, the capillary 160 is a controlled temperature profile construction, such as disclosed in copending and commonly assigned U.S. application Ser. No. 09/957,026, filed Sep. 21, 2001, which is incorporated herein by reference in its entirety. In the controlled temperature profile capillary, the downstream electrode 138 has an electrical resistance sufficient to cause it to be heated during operation of the aerosol generating device, thereby minimizing heat loss at the outlet end (i.e., downstream end) of the capillary tube.

The tube forming the capillary passage can be made entirely of stainless steel or any other suitable electrically conductive materials. Alternatively, the tube can be made of a non-conductive or semi-conductive material incorporating a heater made from an electrically conductive material, such as platinum. Electrodes connected at spaced positions along the length of the tube define a heated region between the electrodes. A voltage applied between the two electrodes generates heat in the heated region of the capillary passage based on the resistivity of the material(s) making up the tube or heater, and other parameters such as the cross-sectional area and length of the heated region. As the fluid flows through the capillary passage into the heated region between the first and second electrodes, the fluid is heated and converted to a vapor. The vapor passes from the heated region of the capillary passage and exits from the outlet end. In some preferred embodiments, the volatilized fluid is entrained in ambient air as the volatilized fluid exits from the outlet, causing the volatilized fluid to form an aerosol such as a condensation aerosol. In a preferred embodiment, the MMAD of the aerosol particle size is about 0.5 to 2.5 μm.

The temperature of the liquid in the capillary passage can be calculated based on the measured or calculated resistance of the heating element. For example, the heating element can be a portion of a metal tube, or alternatively a strip or coil of resistance heating material. Control electronics can be used to regulate the temperature of the capillary passage by monitoring the resistance of the heater.

Resistance control can be based on the simple principle that the resistance of the heater increases as its temperature increases. As power is applied to the heating element, its temperature increases because of resistive heating and the actual resistance of the heater also increases. When the power is turned off, the temperature of the heater decreases and correspondingly its resistance decreases. Thus, by monitoring a parameter of the heater (e.g., voltage across the heater using known current to calculate resistance) and controlling application of power, the control electronics can maintain the heater at a temperature that corresponds to a specified resistance target. One or more resistive elements could also be used to monitor temperature of the heated liquid in cases where a resistance heater is not used to heat the liquid in the capillary passage.

The resistance target is selected to correspond to a temperature that is sufficient to cause heat transfer to the liquid such that liquid is volatilized and expands out the open end of the capillary passage. The control electronics activates the heating, such as by applying for a duration of time pulsed energy to the heater. During and/or after such duration the control electronics determines the real time resistance of the heater using input from the measuring device. The temperature of the heater can be calculated using a software program designed to correlate measured resistance of the heater. In this embodiment, the resistance of the heater is calculated by measuring the voltage across a shunt resistor (not shown) in series with the heater (to thereby determine current flowing to the heater) and measuring the voltage drop across the heater (to thereby determine resistance based on the measured voltage and current flowing through the shunt resistor). To obtain continuous measurement, a small amount of current can be continually passed through the shunt resistor and heater for purposes of making the resistance calculation. Pulses of higher current can be used heat the heater to the desired temperature.

If desired, the heater resistance can be derived from a measurement of current passing through the heater, or by other techniques used to obtain the same information. The control electronics determines whether or not to send an additional duration of energy based on the difference between desired resistance target for the heater and the actual resistance as determined by control electronics.

In a developmental model, the duration of power supplied to the heater was set at 1 millisecond. If the monitored resistance of the heater minus an adjustment value is less than the resistance target, another duration of energy is supplied to the heater. The adjustment value takes into account factors such as, for example, heat loss of the heater when not activated, the error of the measuring device and the cyclic period of the controller and switching device. Because the resistance of the heater varies as a function of its temperature, resistance control can be used to achieve temperature control.

In an embodiment, the capillary passage 160 can be constructed of two or more pieces of 32 gauge, 304 stainless steel tubing. In this embodiment, the downstream electrode can be a 3.5 mm length of 29 gauge tubing, while the upstream electrode may have any geometry that minimizes the resistance of the electrode, such as gold (Au) plated copper (Cu) pins.

The control electronics 120 can control the temperature of the capillary passage 160 by monitoring the resistance of the heater used to heat the capillary passage 160. In an embodiment, the control electronics 120 measures voltage and current in order to calculate the resistance across a length of the capillary passage 160. If the control electronics determines that the calculated resistance is below the target value, the control electronics turns power on (e.g., continuous power or pulsed power) for a selected period of time. Likewise, if the control electronics determines that the resistance is above the target value, the control electronics turns off power for a selected period of time. The control electronics continues to repeat this process until the target resistance for the capillary passage 160 is reached.

In this embodiment, the control electronics 120 may include any processor capable of controlling the resistance of the capillary passage 160 via the electrodes 138 and 140, such as a microchip PIC16F877, available from Microchip Technology Inc., located in Chandler, Ariz., which is programmed in assembly language.

The device can be programmed to achieve various control schemes. For instance, a resistance control scheme can be used to minimize overheating and under heating of the heater arrangement. In particular, a program can be used to send power to the heater until a target resistance value is reached. Under a power control scheme, a certain amount of power is supplied to the heater arrangement and the power is monitored and adjusted to maintain the heater arrangement at a desired temperature. In a voltage control scheme, a certain voltage (e.g., 4 Volts) can be continuously supplied to the heater arrangement and a program (e.g., algorithm) is used to monitor and maintain the voltage at a target value.

As mentioned above, the aerosol generating device can include a pressure sensor. As shown in FIGS. 4 and 5, the pressure sensor 122 is in fluid communication with the mouthpiece 134 via the air passage 132. The air passage 132 includes the air inlet 124 through which ambient air within the housing is drawn into the air passage 132 by a user inhaling on the mouthpiece 134. In a preferred embodiment, the aerosol generating device 100 is activated by a user inhaling on an outlet 144 of the mouthpiece 134. This inhalation causes a differential pressure in the air passage 132, which is sensed by the pressure sensor 122. The pressure sensor 122 can be extremely sensitive. For example, the pressure sensor can be triggered at a selected threshold value of air flow through the air passage 132, for example, as low as about 3 liters/min. This value equals less than about $1/10$ of the typical human inhalation flow rate. Accordingly, the user can trigger the pressure sensor without wasting appreciable lung volume.

Alternatively, the fluid delivery assembly 110 can be activated by a user manually depressing the switch 128, or the fluid delivery assembly 110 can be programmed to provide continuous flow of the liquid aerosol formulation so as to produce a continuous stream of aerosol particles.

The pressure sensor 122 or switch 128 activates the fluid delivery assembly 110 to cause liquid 153 (e.g., a liquid aerosol formulation including a high volatility carrier and a drug) to flow from the liquid source 106 to the capillary passage 160 of the heater unit 130. The fluid is heated in the capillary passage 160 by the heater to a sufficiently high temperature to vaporize the liquid. Ambient air is delivered through the air passage 132 to a condensation region 146 proximate to the outlet end of the capillary passage, at which the vapor is admixed with the ambient air to produce an aerosol such as a condensation aerosol or a non-condensation aerosol.

In alternative embodiments, a pressurized air source can be used with the aerosol generating device to provide dilution air to mix with the aerosol. For example, the pressurized air source can be a compressed air source located within the aerosol generating device (not shown), a fan/blower to flow air into the mouthpiece, or any other suitable device.

The control electronics 120 can perform various selected functions in the aerosol generating device 100. For example, the control electronics 120 can control the temperature profile of the capillary passage 160 during operation of the aerosol generating device 100. The control electronics 120 can also control the output of the display 114. The display is preferably a liquid crystal display (LCD). The display can depict selected information pertaining to the condition or operation of the aerosol generating device 100. The control electronics can also control the operation of the inlet valve 156, discharge member 164 and outlet valve 158 during operation of the aerosol generating device 100; monitor the initial pressure drop caused by inhalation and sensed by the pressure sensor 122; and monitor the condition of the battery unit 116 that provides electrical power to components of the aerosol generating device.

In the embodiment shown in FIG. 4, the battery unit 116 can comprise, for example, one or more rechargeable batteries. The battery unit is preferably rechargeable via the charging jack 118. The battery unit provides power to components of the aerosol generating device (e.g., the control electronics 120, pressure sensor 122, etc.) and the master on/off switch.

The master on/off switch controls powering up and powering down of the aerosol generating device 100 during operation. The master on/off switch also activates the display 114. In an embodiment, the display provides information including, for example, the number of doses remaining within the liquid source 106, the status of the heater unit 130, and a detected low voltage condition of the battery unit 116. The control electronics 120 can also include functionality via the processor for displaying the number of remaining doses, information on patient compliance, lockout times and/or child safety locks.

During operation of the aerosol generating device 100, a user removes the cap 104 to activate components of the aerosol generating device and expose the mouthpiece 134. The user activates switch 128, or inhales on the mouthpiece, which creates a pressure drop in the interior of the mouthpiece. This pressure drop is detected by the pressure sensor 122, which then sends a signal to a controller included in the control electronics 120, which operates the fluid delivery assembly 110.

The metering chamber 162 is filled and emptied by actuation of the discharge member 164. Closing of the discharge member 164 with the inlet valve 156 closed and the outlet valve 158 opened empties liquid in the metering chamber 162, which forces liquid present in the flow passage 150 downstream of the metering chamber into the capillary passage 160. The metering chamber 162 ensures that a desired volume of liquid in aerosol form is delivered by the aerosol generating device 100 to the user. The metering chamber can have a selected dose volume of, e.g., 5 μL. However, the metering chamber can have any desired volume depending upon the application of the aerosol generating device 100. After delivery of the desired volume of the medicament to the capillary passage 160, the outlet valve 158 is closed, and the flow passage 150 is refilled with liquid from the liquid source 106.

During a fill cycle of the aerosol generating device 100, the metering chamber 162 is filled with liquid from the liquid source 106. While the discharge member 164 is opened, the outlet valve 158 is closed and the inlet valve 156 is opened to allow the liquid to fill the metering chamber 162.

During delivery of the liquid to the capillary passage 160, the inlet valve 156 is closed. As the inlet valve 156 closes, the outlet valve 158 is opened, while the discharge member 164 is closed to empty the metering chamber 162 and force liquid from the flow passage 150 into the heated capillary passage 160.

Liquid flows through the heated capillary passage 160 and exits as a vapor. At the exit of the capillary passage 160, ambient air provided via the air passage 132 admixes with vapor in the condensation region 146 to form a condensation or non-condensation aerosol. For example, the second component of the liquid aerosol formulation may be volatilized and condense to form a condensation aerosol.

Preferably, the aerosol particles have a MMAD between about 0.5 μm and about 2.5 μm. However, in some other preferred embodiments, the aerosol particles can have a smaller particle size, such as an MMAD of less than about 0.5 μm, for example, less than about 0.1 μm. As described above, the aerosol generating device can provide aerosols having a controlled particle size, including aerosols sized for the targeted delivery of drugs to the lung. These aerosols offer a number of advantages for delivering drugs to the deep lung. For example, mouth and throat deposition are minimized, while deposition in the deep lung is maximized, especially when combined with a breath hold.

The aerosol generating device preferably generates aerosols in which 95% of the aerosol particles (aerosol droplets) have a size in the range between about 0.5 μm to about 2.5 μm. However, the aerosol can contain aerosol particles smaller than about 0.5 μm, such as, for example, less than about 0.1 μm. When the carrier is ethanol, the preferred aerosol particle size is less than about 0.5 μm. The aerosol generating device preferably incorporates a processor chip for controlling the generation process. The processor, with suitable sensors, also triggers the aerosol generation at any desired time during an inhalation.

Operation of the preferred aerosol generating device for delivering aerosolized medicaments is as follows. First, the liquid aerosol formulation containing at least one high volatility liquid carrier and medicament is delivered to the heated capillary passage. The liquid vaporizes in the capillary passage and exits as a vapor jet from the open end of the capillary passage. The vapor jet entrains and mixes with ambient air and forms a highly concentrated, fine aerosol. As described above, application of heat to vaporize the liquid is preferably achieved by resistive heating from passing an electric current through the heater. The applied power is adjusted to maximize the conversion of the fluid into a vapor.

The aerosol generating device can form aerosols over a range of fluid flow rates dependent on the size of the capillary passage and the power available to vaporize the liquid.

As will be appreciated, the aerosol generating device is capable of controlled vaporization and aerosol formation of drug formulations. The aerosol generating device can provide immediate delivery of aerosol to a patient, thereby not wasting lung capacity, which may be limited due to the health of the patient. Also, the aerosol generating device can provide consistent delivery of controlled amounts of drug formulation to a patient. In addition, in preferred embodiments, the aerosol generated by the aerosol generating device including a capillary passage is only slightly affected by relative humidity and temperature.

In a preferred embodiment, the emitted dose (i.e., the aerosolized dose) can be at least about 75%, preferably about 75%–95%, of the metered dose of the liquid used to produce the aerosol; the respirable fraction of the emitted dose can be at least 75%, preferably about 75%–95%, of the emitted dose; and the variation in the emitted dose can be less than about 5%.

The device can deliver a continuous stream of aerosol particles. For example, the device can generate bulk volumes of particles for use as medicaments, or as components in paints, scents, etc. As disclosed in commonly-assigned U.S. Provisional Patent Application No. 60/308,608, filed Jul. 31, 2001, the device may be operated intermittently, e.g., on demand, or continuously. For example, an aerosol generation rate can be obtained on the order of 140 mg/hr. by flowing a 1% solution of budesonide in ethanol at 5 μL/sec. The bulk volume of budesonide particles typically have a MMAD of 0.04 μm and a geometric standard deviation of 1.8. The aerosol particles can be liquid or solid, depending on the equilibrium phase of the solute (i.e., second component).

EXAMPLES

Example 1

A test was conducted to demonstrate the generation of an aerosol from a liquid aerosol formulation including a high volatility carrier and a solute. A 1% solution of albuterol in ethanol, a high volatility carrier, was heated and vaporized in a heated capillary sized passage of an aerosol generating device. The resulting vapor was admixed with air to form an aerosol. The size distribution of aerosol particles in the aerosol was analyzed with a cascade impactor (model MOUDI from MSP Corporation, Minneapolis, Minn.).

Figure 7:
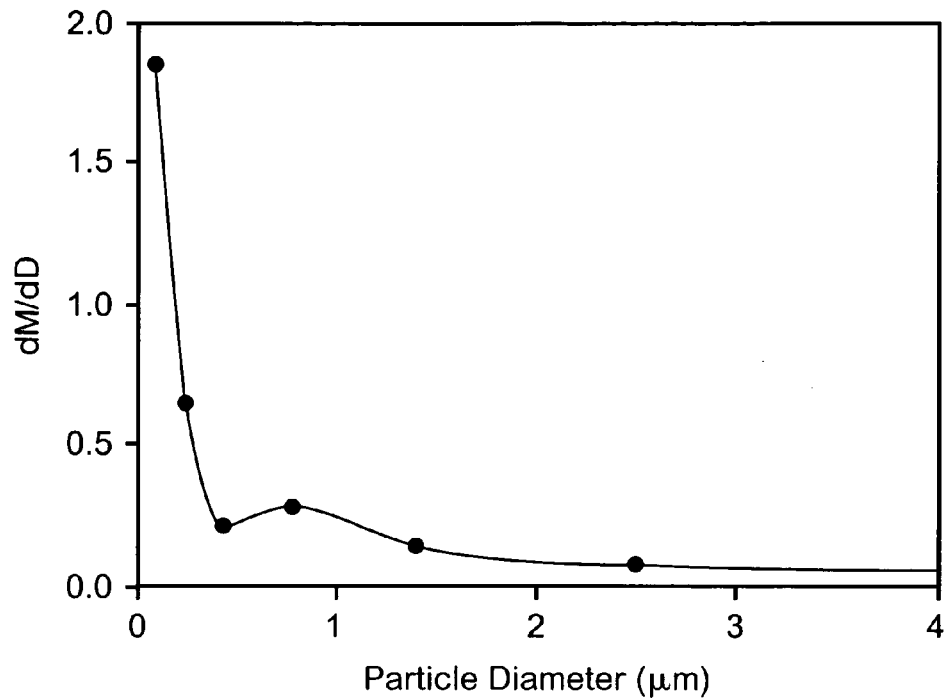
FIG. 7 illustrates the size distribution of aerosol particles of albuterol generated from an ethanol/albuterol solution.

The aerosol particles were determined to be predominantly dry, solid albuterol particles by visually inspecting the plates of the cascade impactor. The measured size distribution of the aerosol particles is shown in FIG. 7. The average MMAD of the aerosol particles was 0.66 microns. The geometric standard deviation ($\sigma_g$) of the aerosol particles was 5.6, which indicates that the aerosol particles had a relatively broad size distribution.

Example 2

Tests were conducted to demonstrate that the aerosol generating device is capable of generating aerosols using a liquid aerosol formulation that includes high volatility carrier and a medicament other than albuterol. Specifically, the liquid aerosol formulation that was used contained ethanol as the carrier and budesonide as the medicament. Recoveries and size distributions of aerosol particles over a range of budesonide concentrations and liquid aerosol formulation flow rates were determined. Solutions of budesonide in ethanol were heated and vaporized in a heated capillary sized passage of an aerosol generating device. The resulting vapor was admixed with air to form an aerosol. The size distribution of aerosol particles in the aerosol was analyzed with an eight-stage cascade impactor (model MOUDI from MSP Corporation, Minneapolis, Minn.).

Tests were conducted using a 0.5% wt./wt. solution of budesonide in ethanol. The aerosol generating device included a 32 gauge, 17 mm long capillary sized passage. The aerosol generation time was 10 seconds. A 500 μL Hamilton syringe in a syringe pump was used as the fluid source to supply the liquid aerosol formulation to the capillary sized passage.

The aerosol particle size distribution determined with the cascade impactor indicated that the MMAD of the aerosol particles was very small. Visual inspection of the plates of the cascade impactor revealed that the deposited aerosol particles were dry budesonide powders. This result using ethanol and budesonide to produce an aerosol is consistent with the production of dry aerosols in Example 1 using ethanol and albuterol.

The diameter of aerosol particles cut by the inlet and eight plates of the cascade impactor and the associated budesonide recovery for each stage, for replicate runs 1–3, are presented in Table 1. The data show that a major portion of the budesonide deposited on the filter in each run, indicating that a major portion of the recovered budeside had a diameter smaller than the cut diameter of the eighth stage (i.e., smaller than 0.18 μm). The data were fit to an assumed lognormal shape and the results are shown in Table 2. The average MMAD of the aerosol for the there runs was 0.06 μm±0.006 μm and the GSD was 3.09±0.49.

TABLE 1

| Stage | Diameter of Aerosol Particles Cut by Stage (μm) | Recovery (%) | | |
|---|---|---|---|---|
| | | Run 1 | Run 2 | Run 3 |
| Elbow | | 5.1 | 6.2 | 8.8 |
| Inlet | 18 | 0 | 0 | 0.9 |
| 1 | 10 | 0 | 0 | 0 |
| 2 | 5.6 | 0 | 0 | 0 |
| 3 | 3.2 | 1.1 | 1.2 | 1.1 |
| 4 | 1.8 | 2.3 | 2.6 | 2.3 |
| 5 | 1.0 | 3.2 | 3.2 | 3.7 |
| 6 | 0.56 | 5.0 | 6.0 | 7.5 |
| 7 | 0.32 | 3.0 | 4.0 | 5.1 |
| 8 | 0.18 | 3.5 | 4.1 | 4.4 |
| Filter | 0 | 44.8 | 38.8 | 36.2 |

TABLE 2

| | Run 1 | Run 2 | Run 3 |
|---|---|---|---|
| MMAD (μm) | 0.05 | 0.06 | 0.06 |
| GSD | 2.6 | 3.1 | 3.6 |

The budesonide aerosol particle recovery data (Tables 1 and 2) shows that a significant percentage of budesonide deposited in the elbow of the apparatus. It is believed that this result may have been due to the formation of large droplets of unvaporized solution, which impacted in the elbow.

Clogging of the capillary size passage of the aerosol generating device was not observed during these tests. In addition, no breakdown products of budesonide were observed during these tests, most likely because of the aerosol generation temperatures that were used.

Example 3

Further tests were performed using a 1% wt./wt. solution of budesonide in ethanol as the liquid aerosol formulation. The aerosol generating device used in these tests included a 28 gauge capillary sized passage having a 25 mm length. A single aerosol particle size determination was made of aerosol produced using the solution. The aerosol particles had an average MMAD of about 0.06 μm with a GSD of about 2.7.

Figure 8:
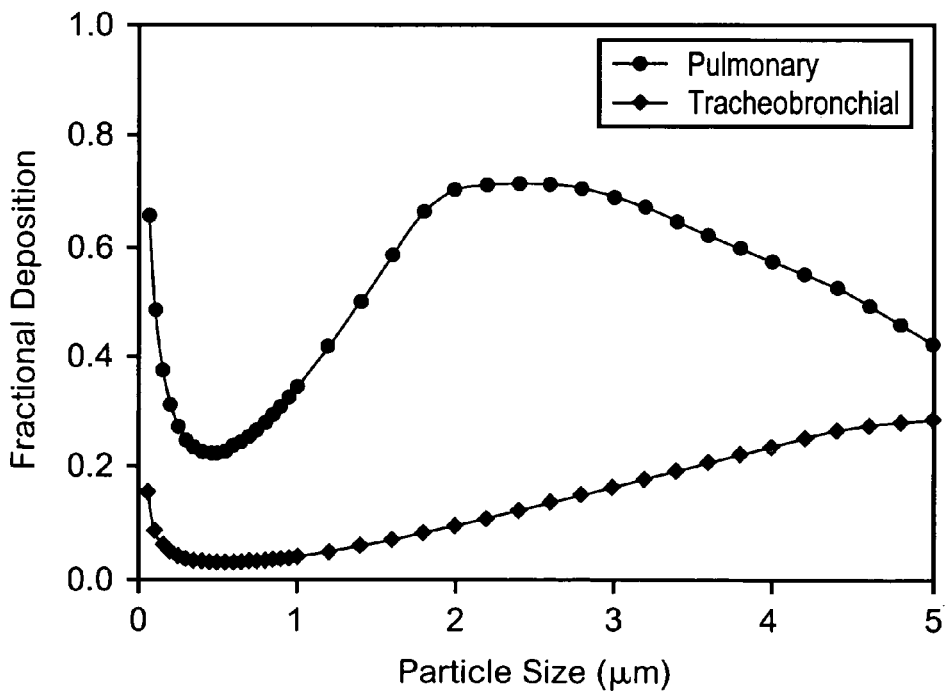
FIG. 8 shows plots of fractional deposition in the pulmonary and tracheobronchial regions of the lung versus aerosol particle size.

The extremely small aerosol particles that were produced by the aerosol generating device using the ethanol/budesonide solutions are highly efficient for delivering medicaments to the deep lung by diffusion. FIG. 8 shows plots of fractional lung deposition in the pulmonary and tracheobronchial regions versus particle size. As shown, the fractional particle distribution is greater in the pulmonary region than the tracheobronchial region over the depicted particle size range of up to 5 microns. FIG. 8 shows that lung deposition is high for very small particles that can be produced using a high volatility carrier, e.g., ethanol as the carrier.

Example 4

Tests were performed to determine effects of the budesonide concentration in the liquid aerosol formulation and the fluid flow rate of the liquid aerosol formulation into the heated capillary sized passage on the size of the aerosol particles produced. Tests were performed using 0.25% and 2.8% wt./wt. solutions of budesonide in ethanol at different flow rates.

Figure 9:
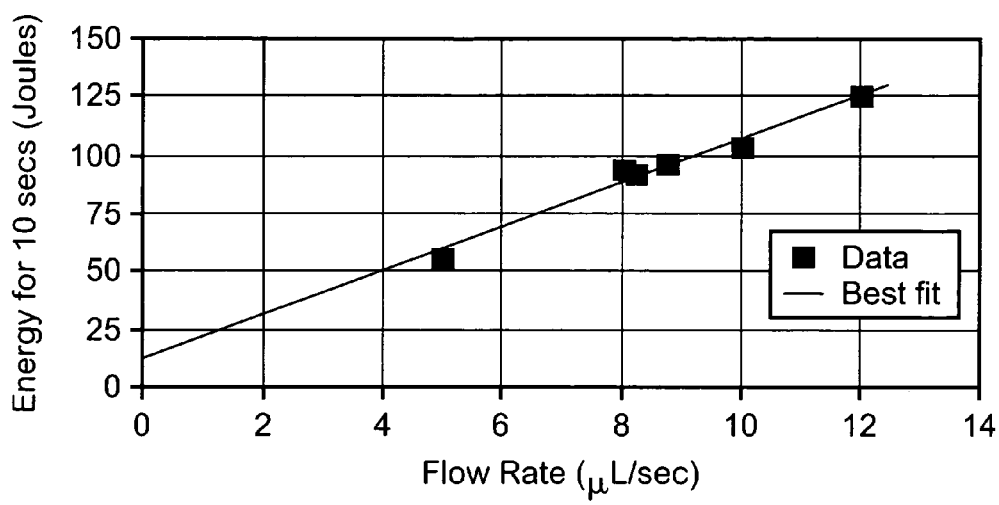
FIG. 9 shows the relationship between energy (applied for 10 seconds to the capillary sized passage) and fluid flow rate for a 2.8% budesonide/ethanol solution.

FIG. 9 shows the relationship between the energy applied to the capillary sized passage (for 10 seconds) for aerosol generation and the fluid flow rate for the 2.8% budesonide solution. The aerosol generating device performed automatic resistance control during operation. The control electronics of the aerosol generating device automatically adjusted the amount of energy delivered to the heater to compensate for changes in the flow rate. FIG. 9 shows the linear relationship between the energy delivered to the heater and flow rate. FIG. 9 also shows that at zero fluid flow, the energy required to keep the heater at the target resistance (due to energy losses) is about 1.3 watts.

Example 5

Three tests were conducted using a ten-stage MOUDI impactor (i.e., two additional final stages were added to the eight-stage device) to provide aerosol particle cuts down to 0.05 μm. Test results for a 2.8% wt./wt. solution of budesonide in ethanol at a fluid flow rate of 5 μL/sec are given in Table 3. Data were fitted to an assumed lognormal curve. Most of the collected aerosol particle mass was on the final filter, even with the addition of the two extra stages. The average MMAD values of the aerosol particles for the three tests were very small; namely, approximately 0.01 μm.

TABLE 3

| | Test 1 | Test 2 | Test 3 |
|---|---|---|---|
| MMAD (μm) | 0.02 | 0.01 | 0.01 |
| GSD | 6.2 | 5.6 | 5.8 |

Example 6

Figure 10:
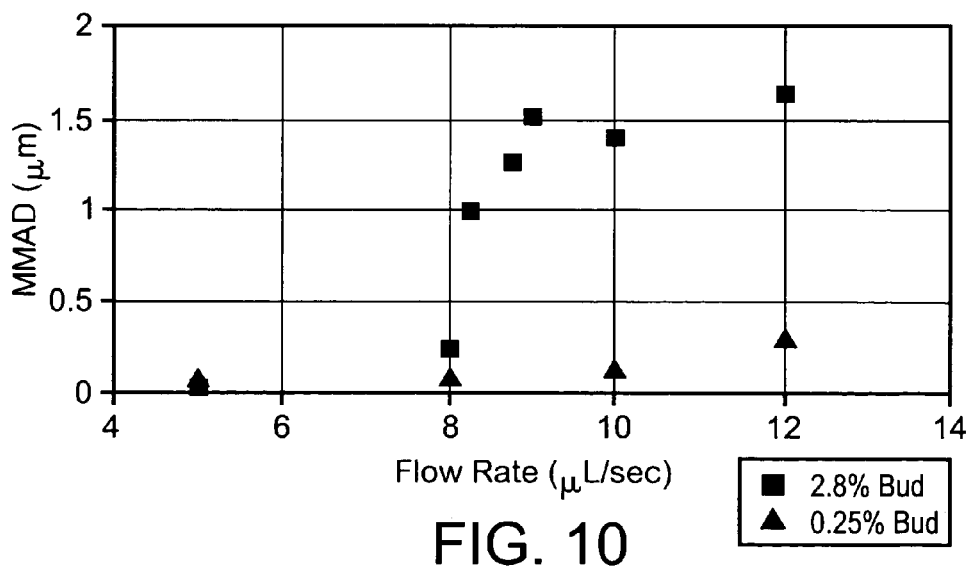
FIG. 10 illustrates the relationship between the MMAD (mass median aerodynamic diameter) of budesonide aerosol particles and fluid flow rate for aerosol generated using 2.8% and 0.25% budesonide in ethanol solutions.

Tests were conducted to evaluate the dependence of the MMAD of aerosol particles produced using ethanol/budesonide solutions on the fluid flow rate of the solutions. Two different solution concentrations were used; namely, 0.25 and 2.8% wt./wt. solutions of budesonide in ethanol. Aerosol particle sizes ranging from less than 0.1 μm to about 1.5 μm were produced at fluid flow rates between 5–12 μL/sec. As shown in FIG. 10, the results for the 2.8% budesonide solution reflected a strong dependence of the MMAD on flow rate, while the aerosol particle size produced using the 0.25% budesonide solution showed significantly less dependence on the flow rate. These test results demonstrate that the particle size of aerosols produced using liquid aerosol formulations containing high volatility carrier, such as ethanol, can be controlled by varying the medicament concentration and/or the fluid flow rate. Namely, at a given fluid flow rate, the concentration of medicament can be varied to control the aerosol particle size, and at a given medicament concentration, the flow rate can be varied to control the aerosol particle size.

Example 7

Figure 11:
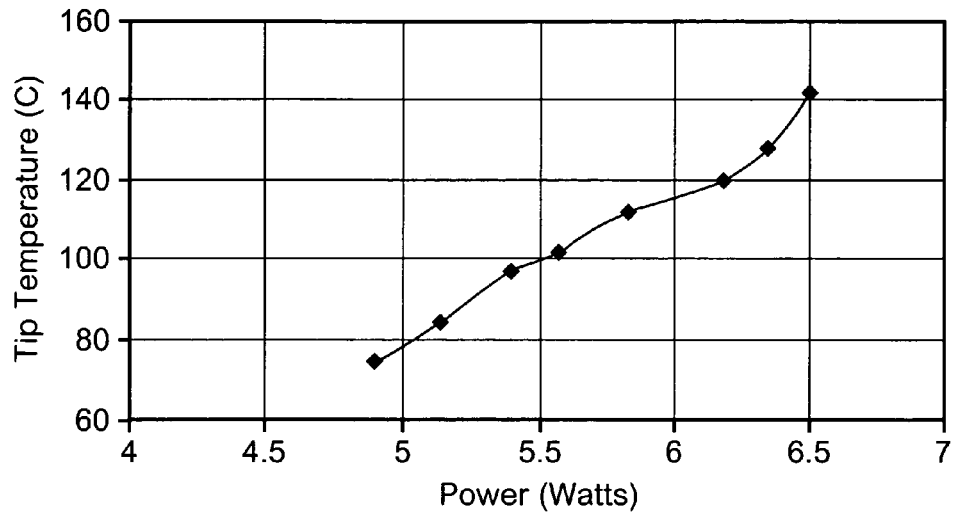
FIG. 11 illustrates the relationship between the tip temperature of a capillary sized passage and applied power.

The relationship between the tip (exit) temperature of the capillary sized passage of the aerosol generating device and the power applied to the capillary sized passage was evaluated. FIG. 11 shows the average tip temperature as a function of the applied power at a flow rate of 5 μL/sec. Ethanol has a boiling point of about 78° C. The optimal tune point of the capillary sized passage with respect to power was about 5.5 Watts, corresponding to a tip temperature of about 100° C. Accordingly, the tip temperature preferably is greater than the boiling point of the carrier.

The above-described test results demonstrate that the aerosol generating device can be used to generate budesonide aerosols with up to 100% recoveries, no observable degradation, and sufficiently small particle sizes for inhalation, using a carrier including ethanol. In addition, the test results demonstrate that the aerosol particle size can be controlled by varying the medicament concentration and/or fluid flow rate of the liquid aerosol formulation.

Example 8

Figure 12:
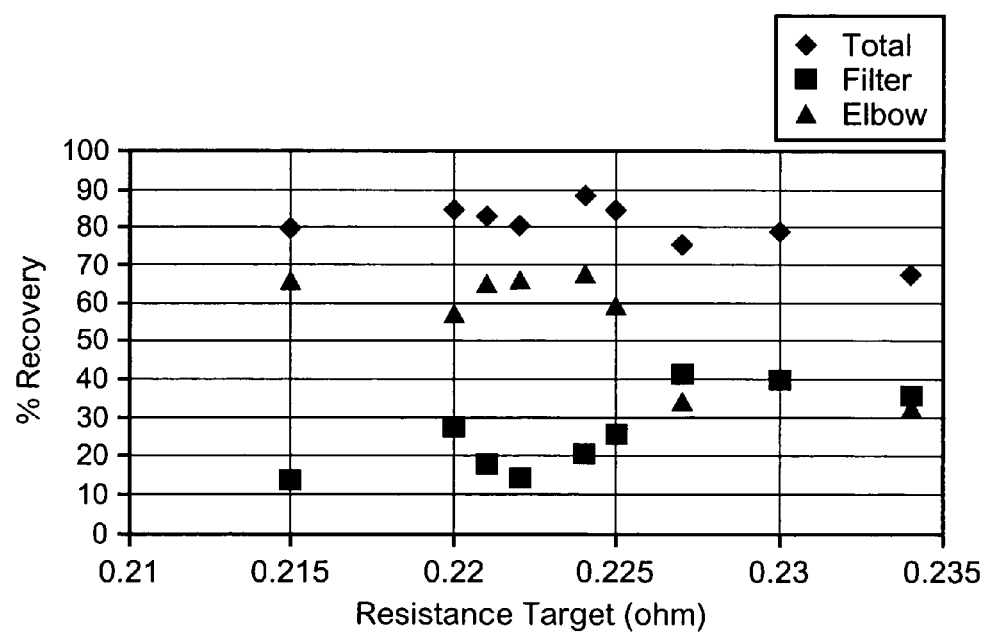
FIG. 12 illustrates the % recovery of albuterol sulfate for a 1% solution of albuterol sulfate in water at a fluid flow rate of 5 µL/sec.

Tests were conducted to demonstrate that the aerosol generating device is also capable of generating aerosols using water as the high volatility carrier. FIG. 12 shows the percent recovery of albuterol sulfate for a 1 weight % solution of albuterol sulfate in water at a solution flow rate of 5 μL/sec using a 26 gauge capillary sized passage having a length of 21 mm. The results indicate that about 40% of the albuterol sulfate was recovered on the filter and about 40% was deposited in the elbow.

Example 9

Figure 13:
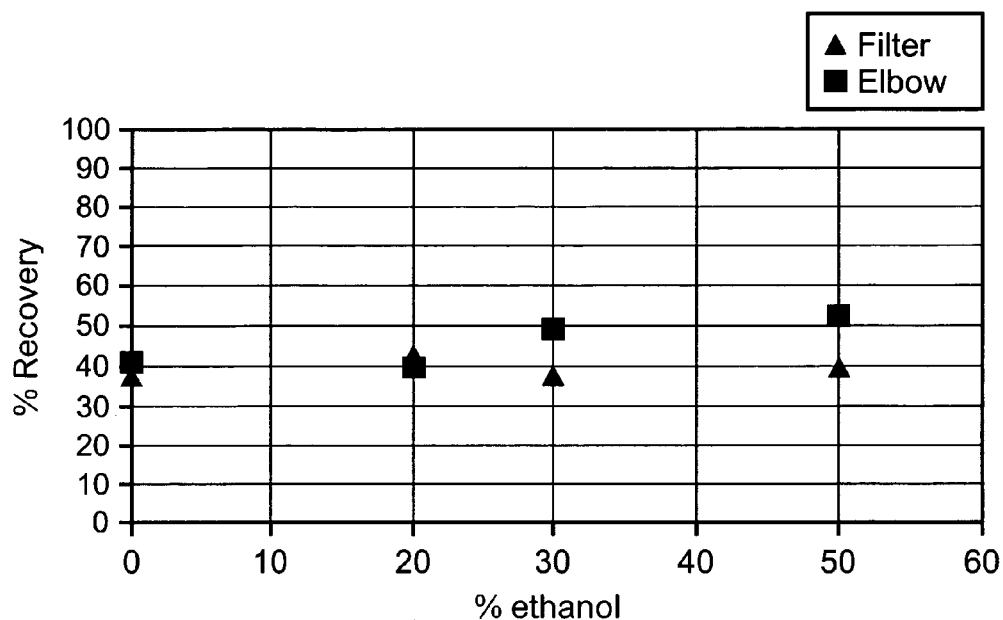
FIG. 13 illustrates the % recovery of albuterol for albuterol solutions containing varying percentages of ethanol and water.

Tests were also conducted to determine the effect on the albuterol particle size distribution and MMAD when ethanol is added to the albuterol/water solution used in Example 8. That is, two high volatility carriers, water and ethanol, were used as the carrier. FIG. 13 shows the recovery of albuterol in the albuterol/ethanol/water system at different volume percentages of ethanol in the carrier ranging from 0 volume % ethanol (i.e., 100 volume % water) to 50 volume % ethanol (i.e., 50 volume % water). Increasing the volume percentage of ethanol (decreasing the volume percentage of water) in the carrier increased the recovery of albuterol.

Figure 14:
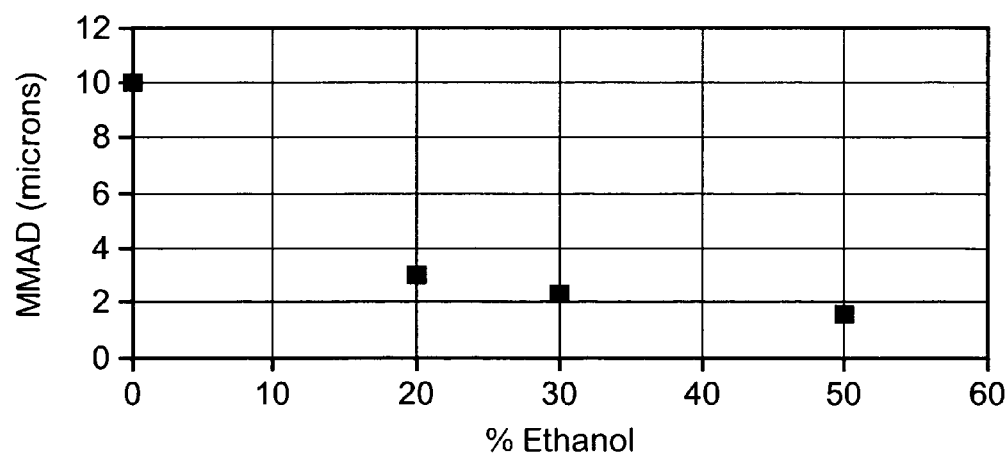
FIG. 14 illustrates the MMAD of albuterol aerosol particles versus volume % ethanol for albuterol solutions containing varying volume percentages of ethanol and water.

The effect of varying the percentage of ethanol in the carrier on the albuterol MMAD for up to 50 volume % ethanol additions was also investigated. FIG. 14 shows that increasing the percentage of ethanol in the carrier decreased the MMAD of albuterol in the aerosol.

Figure 15:
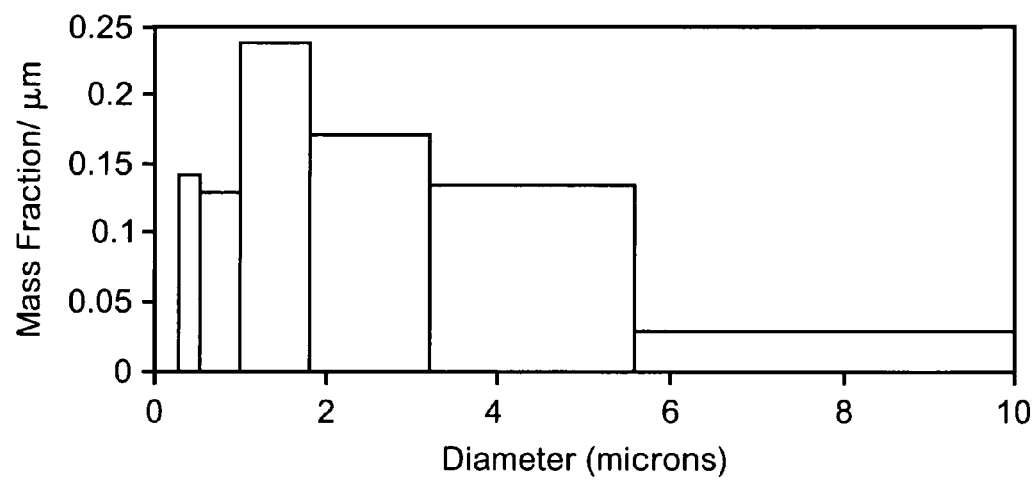
FIG. 15 shows the relationship between mass fraction and diameter for albuterol aerosol particles generated using a liquid aerosol formulation containing a 20 volume % ethanol-water solution as the carrier.

FIG. 15 shows the relationship between the aerosol particle mass fraction versus the aerosol particle diameter for a 20 volume % ethanol in water solution used as the carrier. As shown, the particle size distribution of albuterol was relatively narrow. The average MMAD of the albuterol aerosol particles was about 3 microns, which is a desirable size for deposition in the human lung. The albuterol recovery was about 47%.

Albuterol aerosol particles produced using a carrier containing varying percentages of ethanol in water as described above were visually analyzed and determined to be dry aerosols.

The Example test results demonstrate that aerosols containing particles of micron and sub-micron diameters can be produced from liquid aerosol formulations containing a selected aerosol-forming component and one or more high volatility carriers. The aerosols can be produced using various aerosol-forming components, such as albuterol and budesonide, and one or more high volatility carriers. In a preferred embodiment, the aerosols produced from the liquid aerosol formulation are dry aerosols that contain aerosol particles that are substantially dry particles of the component (i.e., the aerosol particles contain substantially no liquid resulting from conversion of the high volatility carrier to an aerosol).

Furthermore, the test results demonstrate that aerosols containing aerosol particles having micron and sub-micron diameters can be produced from liquid aerosol formulations containing a selected aerosol-forming component and a carrier, which contains at least one high volatility carrier, such as ethanol, or ethanol and water. Alternatively, the high volatility carrier can be water alone. Aerosols produced using a water-containing carrier preferably are dry aerosols that contain aerosol particles consisting essentially of dry particles of the aerosol-forming component.

Producing dry aerosols using at least one high volatility carrier and at least one other component can provide the capability of delivering dry powders of aerosol particles without requiring additional steps, such as heating the particles to keep the powder dry; reduced particle agglomeration; and/or provide powder entrainment in fluid streams.

The aerosols produced from the liquid aerosol formulations using high volatility carriers can be used in a variety of applications including, for example, the controlled generation of fine particles of medicaments for targeted delivery to the lungs via inhalation; the preparation of finely divided medications; the controlled (continuous or non-continuous) generation of fine particles for industrial uses; and the production of jets of fine particles for coating objects.

The above-described exemplary modes are not intended to be limiting. It will be apparent to those of ordinary skill in the art that modifications thereto can be made without departure from the spirit and scope as set forth in the accompanying claims. For instance, while a heated capillary tube has been described as the preferred construction of the capillary passage, the capillary passage can comprise one or more channels in a laminate having a heater arranged along the channel(s), multiple capillary tube arrangements, a passage having a heater located inside the passage, coaxial arrangements including an annular channel for fluid flow, or the like.

What is claimed is:

1. An aerosol generating device, comprising:
   a liquid source of a liquid aerosol formulation comprising a high volatility carrier and a second component;
   a flow passage in fluid communication with the liquid source; and
   a heater disposed to heat liquid aerosol formulation in a heated portion of the flow passage to produce a vapor which admixes with air to produce an aerosol.

2. The aerosol generating device of claim 1, wherein the carrier is ethanol.

3. The aerosol generating device of claim 1, wherein the second component is a medicament.

4. The aerosol generating device of claim 3, wherein the medicament is at least one member selected from the group consisting of analgesics; anginal preparations; anti-allergics; antibiotics; anti-convulsants; antidepressants; antiemetics; antihistamines; antiparkisonian drugs; antipsychotics; antitussives; anxiolytics; bronchodilators; diuretics; anticholinergics; hormones and anti-flammatory agents; drugs for erectile dysfunction; drugs for migraine headaches; drugs for the treatment of alcoholism; drugs for the treatment of addiction; muscle relaxants; nonsteroidal anti-inflammatories and opioids.

5. The aerosol generating device of claim 1, wherein the second component is albuterol or budesonide.

6. The aerosol generating device of claim 1, wherein the second component is dissolved in the carrier.

7. The aerosol generating device of claim 1, wherein the liquid aerosol formulation is propellant free.

8. The aerosol generating device of claim 1, wherein the aerosol comprises aerosol particles that consist essentially of the second component.

9. The aerosol generating device of claim 1, wherein the aerosol is a condensation aerosol.

10. The aerosol generating device of claim 1, wherein the aerosol particles consist essentially of substantially dry solid particles.

11. The aerosol generating device of claim 1, further corn p rising:
 a power supply; and
 a controller operable to deliver power from the power supply to the heater so as to maintain the heater at a temperature range effective to vaporize the liquid aerosol formulation in the flow passage.

12. The aerosol generating device of claim 11, further comprising at least one valve disposed between the liquid source and the flow passage, the controller is operable to actuate the valve to open and close the flow passage to control flow of the liquid aerosol formulation from the liquid source to the flow passage.

13. The aerosol generating device of claim 11, further comprising:
 a mouthpiece through which the aerosol is inhaled by a user of the aerosol generating device;
 a pressure sensor;
 an air passage through which air is supplied into the mouthpiece; and
 a valve which opens and closes the air passage;
 wherein the controller is operable to actuate the valve within a predetermined time period after the pressure sensor detects a pressure drop in the mouthpiece as the user inhales on the mouthpiece to allow air to be supplied into the mouthpiece.

14. The aerosol generating device of claim 1, wherein the flow passage comprises a metering chamber having a predetermined volume, and the aerosol generating device comprises a discharge member operable to deliver an amount of the liquid aerosol formulation equal to the predetermined volume into the heated portion of the flow passage.

15. The aerosol generating device of claim 1, which is a hand held inhaler.

16. The aerosol generating device of claim 1, wherein the liquid source, flow passage and heater comprise a fluid delivery assembly which is removably attached to the aerosol generating device.

17. An aerosol generating device, comprising:
 a liquid source of a liquid aerosol formulation comprising a carrier and albuterol or budesonide;
 a flow passage in fluid communication with the liquid source; and
 a heater disposed to heat liquid aerosol formulation in a heated portion of the flow passage to produce a vapor which admixes with air to produce an aerosol.

18. A method of generating an aerosol, comprising:
 (a) supplying a liquid aerosol formulation comprising a high volatility carrier and a second component from a liquid source to a flow passage;
 (b) heating liquid aerosol formulation in a heated portion of the flow passage to produce a vapor; and
 (c) admixing the vapor with air to produce an aerosol.

19. The method of claim 18, wherein the carrier comprises ethanol.

20. The method of claim 18, wherein the second component is a medicament.

21. The method of claim 20, wherein the medicament is at least one member selected from the group consisting of analgesics; anginal preparations; anti-allergics; antibiotics; anti-convulsants; antidepressants; antiemetics; antihistamines; antiparkisonian drugs; antipsychotics; antitussives; anxiolytics; bronchodilators; diuretics; anticholinergics; hormones and anti-flammatory agents; drugs for erectile dysfunction; drugs for migraine headaches; drugs for the treatment of alcoholism; drugs for the treatment of addiction; muscle relaxants; nonsteroidal anti-inflammatories and opioids.

22. The method of claim 18, wherein the second component is albuterol or budesonide.

23. The method of claim 18, wherein the second component is dissolved in the carrier.

24. The method of claim 18, wherein the liquid aerosol formulation is propellant free.

25. The method of claim 18, wherein the aerosol comprises aerosol particles that consist essentially of the second component.

26. The method of claim 18, wherein the aerosol is a condensation aerosol.

27. The method of claim 18, wherein the aerosol particles consist essentially of substantially dry solid particles.

28. The method of claim 18, wherein aerosol particles of the aerosol have a mass median aerodynamic diameter of less than 2.5 microns.

29. The method of claim 18, wherein the flow passage is a capillary sized flow passage.

30. The method of claim 18, further comprising:
 supplying a predetermined volume of the liquid aerosol formulation into the heated portion of the flow passage; and
 heating the predetermined volume of the liquid aerosol formulation to produce the vapor.

31. The method of claim 18, wherein (a)–(c) are performed using an aerosol generating device comprising a mouthpiece, the method further comprising:
 detecting a pressure drop in the mouthpiece of the aerosol generating device caused by a user inhaling on the mouthpiece;
 supplying a predetermined volume of the liquid aerosol formulation into the heated portion of the flow passage after detecting the pressure drop; and
 delivering the aerosol to the user through the mouthpiece.

32. The method of claim 18, comprising producing the aerosol continuously.

33. The method of claim 18, further comprising:
 performing (a)–(c) using a first fluid delivery assembly attached to an aerosol generating device;
 removing the first fluid delivery assembly from the aerosol generating device;
 attaching a second fluid delivery assembly to the aerosol generating device; and
 repeating (a)–(c) using the second fluid delivery assembly.

34. The method of claim 33, wherein the first fluid delivery assembly supplies a first liquid aerosol formulation, and the second fluid delivery assembly supplies a second liquid aerosol formulation different from the first liquid aerosol formulation.

35. The method of claim 33, comprising producing a first aerosol containing aerosol particles having a first mass median aerodynamic diameter with the first fluid delivery assembly, and producing a second aerosol containing aerosol particles having a second mass median aerodynamic diameter different from the first mass median aerodynamic diameter with the second fluid delivery assembly.

36. A method of generating an aerosol, comprising:
(a) supplying a liquid aerosol formulation comprising a carrier and albuterol or budesonide from a liquid source to a flow passage;
(b) heating the liquid aerosol formulation in a heated portion of the flow passage to produce a vapor; and
(c) admixing the vapor with air to produce an aerosol.

37. The method of claim 18, wherein the liquid aerosol formulation comprises (i) about 20–80 volume % water and about 80–20 volume % ethanol or (ii) about 80–100 volume % water and up to about 20 volume % ethanol.

38. The method of claim 18, wherein the high volatility carrier comprises ethanol and the liquid aerosol formulation comprises at least about 1 weight % budesonide.

39. The method of claim 18, wherein:
the high volatility carrier comprises ethanol;
the second component is albuterol; and
the aerosol comprises aerosol particles have a mass median aerodynamic diameter of about 0.01–0.1 micron.

40. The method of claim 36, wherein the carrier comprises ethanol.

41. The method of claim 36, wherein the carrier comprises (i) about 20–80 volume % water and about 80–20 volume % ethanol or (ii) about 80–100 volume % water and up to about 20 volume % ethanol.

42. The method of claim 36, wherein:
the carrier comprises ethanol; and
the aerosol comprises aerosol particles have a mass median aerodynamic diameter of about 0.01–0.1 micron.

* * * * *